United States Patent
Kross et al.

(10) Patent No.: US 6,599,432 B2
(45) Date of Patent: Jul. 29, 2003

(54) METHODS FOR DISINFECTING SMALL DIAMETER WATER LINES

(76) Inventors: Robert D. Kross, 2506 Florin Ct., Bellmore, NY (US) 11710; William Wade, 5 King Henry Mews, Orpington Kent BR6 6NP (GB)

( * ) Notice: Subject to any disclaimer, the term of this patent is extended or adjusted under 35 U.S.C. 154(b) by 0 days.

(21) Appl. No.: 09/847,493

(22) Filed: May 2, 2001

(65) Prior Publication Data

US 2002/0195406 A1 Dec. 26, 2002

(51) Int. Cl.⁷ .................................................. C02F 1/76
(52) U.S. Cl. ........................ 210/754; 210/764; 422/37; 424/661; 433/80
(58) Field of Search .............................. 210/754, 764; 422/37; 424/661, 662; 433/80, 82

(56) References Cited

U.S. PATENT DOCUMENTS

| | | | | |
|---|---|---|---|---|
| 4,084,747 | A | 4/1978 | Alliger | 239/4 |
| 4,330,531 | A | 5/1982 | Alliger | 424/149 |
| 4,847,089 | A | 7/1989 | Kramer et al. | 424/405 |
| 4,891,216 | A | 1/1990 | Kross et al. | 424/78 |
| 4,929,365 | A | * 5/1990 | Clark et al. | 210/754 |
| 4,941,989 | A | 7/1990 | Kramer et al. | 252/102 |
| 4,956,184 | A | 9/1990 | Kross | 424/661 |
| 4,986,990 | A | 1/1991 | Davidson et al. | 424/665 |
| 5,100,652 | A | 3/1992 | Kross et al. | 424/53 |
| 5,185,161 | A | 2/1993 | Davidson et al. | 424/665 |
| 5,204,004 | A | 4/1993 | Johnston et al. | 210/651 |
| 5,320,624 | A | 6/1994 | Kaplan et al. | 606/77 |
| 5,320,805 | A | 6/1994 | Kramer et al. | 422/28 |
| 5,351,892 | A | 10/1994 | Conte | 239/304 |
| 5,360,338 | A | 11/1994 | Waggoner | 433/80 |
| 5,370,534 | A | 12/1994 | Wolf et al. | 433/80 |
| 5,384,134 | A | 1/1995 | Kross et al. | 424/661 |
| 5,389,390 | A | 2/1995 | Kross | 426/332 |
| 5,474,451 | A | 12/1995 | Dalrymple et al. | 433/80 |
| 5,526,841 | A | * 6/1996 | Detsch et al. | 134/102.2 |
| 5,556,279 | A | 9/1996 | Wolf et al. | 433/82 |
| 5,597,561 | A | 1/1997 | Kross | 424/78.07 |
| 5,620,527 | A | 4/1997 | Kramer et al. | 134/2 |
| 5,628,959 | A | 5/1997 | Kross | 422/37 |
| 5,651,977 | A | 7/1997 | Kross | 424/419 |
| 5,709,545 | A | 1/1998 | Johnston et al. | 433/80 |
| 5,709,546 | A | 1/1998 | Waggoner | 433/82 |
| 5,731,275 | A | 3/1998 | Prevost et al. | 510/161 |
| 5,749,726 | A | 5/1998 | Kinsel | 433/80 |
| 5,759,970 | A | 6/1998 | Prevost et al. | 510/161 |
| 5,772,985 | A | 6/1998 | Kemp et al. | 424/45 |
| 5,785,523 | A | * 7/1998 | Overmyer | 422/28 |
| 5,820,822 | A | 10/1998 | Kross | 422/37 |
| 5,824,243 | A | 10/1998 | Contreras | 261/36.1 |
| 5,837,204 | A | 11/1998 | Prevost et al. | 422/105 |
| RE36,064 | E | 1/1999 | Davidson et al. | 424/665 |
| 5,942,125 | A | 8/1999 | Engelhard et al. | 210/748 |
| 5,942,480 | A | 8/1999 | Prevost et al. | 510/161 |
| 5,961,326 | A | 10/1999 | Johnston et al. | 433/80 |
| 5,971,757 | A | 10/1999 | Selzer et al. | 433/80 |
| 5,972,238 | A | * 10/1999 | Rimpler et al. | 252/187.21 |
| 6,019,905 | A | * 2/2000 | Waggoner | 210/739 |
| 6,040,283 | A | 3/2000 | Miner | 510/461 |
| 6,054,030 | A | * 4/2000 | Pierangela et al. | 204/404 |
| 6,063,425 | A | 5/2000 | Kross et al. | 426/335 |
| 6,096,350 | A | 8/2000 | Kemp et al. | 424/661 |
| 6,099,881 | A | 8/2000 | Hanson | 426/263 |
| 6,106,771 | A | 8/2000 | Fitton | 422/14 |
| 6,117,285 | A | 9/2000 | Welch et al. | 510/461 |
| 6,123,966 | A | 9/2000 | Kross | 424/665 |
| 6,331,514 | B1 | * 12/2001 | Wurzburger et al. | 134/3 |
| 6,424,868 | B1 | * 7/2002 | Smith et al. | 607/59 |

* cited by examiner

*Primary Examiner*—Peter A. Hruskoci
(74) *Attorney, Agent, or Firm*—Henry D. Coleman; Coleman Sudor Sapone, P.C.

(57) ABSTRACT

The present invention is directed to disinfecting compositions for dental unit water lines, particularly effective against microbial flora in biofilms which form on the luminal walls of the piping and reservoir components of dental equipment, as well as methods related to the use of such compositions to reduce microbial numbers in water-bearing dental and other equipment and maintain reduced levels on a continuous basis.

17 Claims, No Drawings

METHODS FOR DISINFECTING SMALL DIAMETER WATER LINES

FIELD OF THE INVENTION

This invention relates generally to the disinfection of dental water unit lines, using aqueous chlorine dioxide solutions, and more particularly to the reduction and destruction of bacteria in biofilms which form on the inner walls of such water lines.

BACKGROUND OF THE INVENTION

The dental profession is becoming increasingly aware, and concerned, that small diameter pipes carrying fresh water from operatory equipment to their patients are contaminated by bacteria and other microorganisms contained in the water flowing through them. Some of the microorganisms inevitably adhere to the inner walls of the pipes and accumulate together with microscopic sediments or other substances into what is commonly known as a biofilm. The biofilm quickly and tenaciously coats the inner walls of the pipes. As it grows, it absorbs nutrients from the water, becoming a culture medium for more microorganisms. These films are typically 30–50 microns thick, and the microbes are distributed throughout the biofilm matrix. Many different types of micro-organism are found in these films including bacteria, fungi, algae and amoebae.

The bacteria found in biofilm are primarily of environmental origin such as Bacillus, Pseudomonas and related genera, and Corynebacterium, but can include organisms from dental patients which are capable of causing serious human infections such as Legionella. There have also been reports of the isolation of human oral bacteria, presumably from back-flow through dental instruments attached to the water line. Sloughing off of microbial aggregates from these biofilms into the lumen will result in bacterial populations reaching alarming levels in the water discharge from the dental instruments connected to the fresh water line. The average bacteria count in the water discharge of dental instruments is approximately 200,000 [$2\times10^5$] colony forming units per milliliter (cfu/ml) and in some extreme cases can reach 10,000,000 [$10^7$] cfu/ml. This is of particular concern since dentists, dental surgeons and dental hygienists, as well as many of their patients, are well aware of the importance of meticulously sterilizing dental instruments to minimize bacterial contamination of these patients. In particular, since dental instruments are used directly in a patient's mouth, when bleeding may sometimes occur as a result of a dental procedure, it is of paramount importance to minimize the presence of microorganisms carried by dental instruments. The microorganisms can of course range from relatively harmless bacteria to dangerous pathogens. Thus, efforts are continuously made to remove microorganisms from dental instruments and from the fresh water lines feeding dental instruments. These include such equipment as air/water guns, high speed water turbines and ultrasonic tartar removers. Where applicable, thermal sterilization remains one of the best methods for eradicating the presence of microorganisms, such as for most hand held dental instruments. However, thermal sterilization is obviously not practical for the decontamination of fresh water lines, which continue to be inordinately difficult to clean, and maintain free from microorganisms.

Many efforts have been expended to accomplish this reduction/destruction, although none has proved completely satisfactory. For example, in the most obvious approach, it has been suggested to use sterile water, particularly to drain the fresh water lines during periods of non-use. Or, as taught in U.S. Pat. Nos. 5,360,338, 5,824,323, and 5,942,125 to create sterile water in the equipment itself, such as by ozonization. Besides the expense, the considerable effort to accomplish these complex operations makes such procedures realistically unacceptable. It is also known that a detergent such as polyoxyethylene sorbitan monooleate (Tween 80™) at approximately 4% dislodges biofilm from small diameter water lines used in dental equipment. However, the use of detergent alone does not effectively destroy the microorganism population. Even the teachings of U.S. Pat. No. 5,942,480, combining detergent, denaturing agent and antimicrobials have not been adopted by dental practitioners as being an effective solution to the elimination of bacterial biofilm.

A number of patents, such as U.S. Pat. Nos. 5,971,757, 5,961,326, 5,749,726, and 5,204,004 teach the use of a variety of replaceable in-line water filters to trap bacteria, such as from biofilm sloughing. These approaches have been found to be impractical, generally because of rapid clogging of the filters whose pore-sizes are sufficiently small to trap bacteria, and which also trap shed biofilm fragments and scale. Since the biofilms in the water lines continue to build up, even in the presence of disinfecting agents, none of those methods has been shown to effectively remedy the microorganism proliferation for any length of time.

It is also known in the art that disinfectants, such as povidone-iodine at a concentration of approximately 10%, reduce the number of microorganisms in small diameter water lines. It is further known from U.S. Pat. No. 5,942,480 that a mixture of mandelic and lactic acids reduces the number of susceptible microorganisms in contaminated tubing. However, such disinfection is somewhat superficial since it fails to effectively attack and destroy the microorganisms found in the biofilm. Consequently, the disinfection effect is short-lived. After 24 hours of treatment with povidone-iodine, the numbers of bacteria are greatly reduced but quickly begin to rise after eight days. Related systems, such as those using iodinated ion-exchange resins, as in U.S. Pat. Nos. 5,556,279 and 5,320,624, also suffer from the same problem, i.e. the inability to penetrate the biofilm and destroy the resident organisms.

In an effort to penetrate and remove biofilms and related deposits, the Ultra-Kleen™ company markets a product based on an alkaline peroxide and a phase transfer catalyst, as taught in U.S. Pat. Nos. 4,847,089 4,941,989, 5,320,805 and 5,620,527. The product makes a claim as a specialty cleaner for dental unit water lines, rather than a more stringent disinfectant or sterilant. Several more potent germicides have been evaluated, including bleach and acidified bleach (U.S. Pat. No. 6,019,905), glutaraldehyde and an alkaline glutaraldehyde-phenolic disinfectant (U.S. Pat. No. 6,040,283), cetyl pyridinium chloride, peracetic acid, chlorhexidine and isopropanol. A recent report in the Journal of the American Dental Association (January, 1999) showed that 15-hours contact with household bleach (5.25%), glutaraldehyde (3%), or isopropanol (15.3%) resulted in effluents from biofilms that were free of recoverable bacteria, but that recolonization returned to pretreatment levels by day 3 for glutaraldehyde, day 6 for bleach, and day 15 for isopropanol. The report stated that the residual effect of these agents raises concerns about the slow release of potentially toxic substances from the residual biofilm matrix into water reaching the dental patient. Furthermore, while the agents temporarily reduce microorganisms in effluent water, they do little to destroy the biofilm matrix in the water lines, even with periodic treatments. A subsequent article suggested that weekly treatment with 5000 ppm chlorine (diluted bleach) coupled with the use of 3 ppm chlorinated water in the dental unit consistently attained the desired bacterial level of <200 cfu/ml. Two concerns arise however with this approach. One is that chlorine has been shown to elevate levels of trihalomethanes (THMs) and other chlorinated byproducts in water, where the EPA has placed limits on THMs in water. Additionally chlorine is a strong oxidant, and causes corrosion of most metals used in operatory equipment. While a 3 ppm level is of little concern, chlorine at the 5000 ppm level has significant corrosion potential for components of expensive dental equipment.

A so-called Stabilized Chlorine Dioxide (SCD) mouthrinse has recently been evaluated for the decontamination of the water lines of ultrasonic scaling units in dental operatories (Wirthlin et al., *J Periodontol.*, 2001, 72:401–410). Although the article title refers to the use of a 0.1% chlorine dioxide/0.5% sodium phosphate mouthrinse, a later reference in the paper correctly describes the product as a stabilized chlorine dioxide formulation. This has been confirmed by both the label on the product, CloSYSII, which lists stabilized chlorine dioxide in the ingredients, and by analysis of the product, which revealed the lack of any detectable chlorine dioxide (i.e. it had below 0.5 parts per million [ppm]), despite the publication's reference to 1000 ppm (0.1%) of chlorine dioxide in the rinse. As is usual for SCD products, which are in fact stabilized chlorite solutions, the sodium chlorite concentration of the product was found to be predominant, at 0.173%, corresponding to 0.129% of chlorite ion. The assumption with SCD products is that conversion to $ClO_2$ from chlorite (i.e. $ClO_2^-$) is 80% efficient, via the chlorous acid route, so the result of 80%× 0.129% chlorite, or 0.102% "chlorine dioxide" is consistent with the nominal 0.1% chlorine dioxide in the product. In the results of the paper on ultrasonic scaling unit waterline decontamination, the decrease of biofilm bacteria following 30 minutes of contact with the SCD was insufficient to offer much promise, amounting to less than 1-log cfu/ml of bacterial reduction, as compared with water flushing along. Specifically there was a 3–5 fold reduction with tap water flushing, and 12–20 fold reduction with the SCD. For dental water lines typically delivering 3–5 logs/cfu of organisms in their water, from resident biofilms, the reduction offered by the chlorite mouthrinse is markedly insufficient for alleviating this pervasive problem.

Accordingly there remains a long-felt need for compositions and their methods for use to decontaminate small diameter water lines for dental equipment and effectively dislodge and eliminate adherent biofilms. At the same time such desired compositions and methods will destroy the microorganism flora in the fresh water and in the dislodged biofilm without concomitant adverse effects on dental equipment, or formation of potentially harmful substances in the water which reaches the patient. There is a more particular need to identify compositions and their methods of use which are compatible with current dental operatory practice, so as to minimally interfere with normal procedures. And, at the same time they should provide the reassurance to the dental professional that the water effluent from such dental units poses no risk from unwanted pathogens or chemical residues or transformation products derived from the decontaminating antimicrobials.

OBJECTS OF THE INVENTION

It is an object of the present invention to provide compositions and methods which can be used to decontaminate small diameter water lines for dental equipment and effectively dislodge and eliminate adherent biofilms.

It is also an object of the present invention to provide such desired compositions and methods which will destroy the microorganism flora in the fresh water and in the dislodged biofilm without concomitant adverse effects on dental equipment, or formation of potentially harmful substances in the water which reaches the patient.

It is also an object of the present invention to provide means for safely destroying microbial-laden biofilms, and ensuring water supplies to the patient that are consistently pathogen and contaminant free.

Any one of these and/or other objects of the invention may be readily gleaned from a reading of the description of the invention which follows.

SUMMARY OF THE INVENTION

In brief, the present invention is directed to disinfecting compositions for dental unit water lines, particularly effective against biofilms which form on the luminal walls of the piping and reservoir components of dental equipment, as well as methods related to the use of such compositions to reduce microbial numbers in water-bearing dental equipment and maintain reduced levels on a continuous basis.

Compositions according to the present invention in a decontamination embodiment comprise an effective amount of chlorine dioxide within the range of about 100 ppm (parts per million) to about 2,500 ppm, preferably within the range of about 250 ppm to about 1,500 ppm, more preferably about 500 ppm to about 1,000 ppm and about 1 ppm to about 10 ppm when used in a maintenance regimen. Methods according to the present invention comprise exposing contaminated dental unit water lines to an effective amount of a chlorine dioxide solution comprising chlorine dioxide within the range of about 100 ppm to about 2,500 ppm and for a period of time effective to reduce microbial growth in biofilm lining the dental unit water lines.

The present invention also relates to methods for treating biofilms in dental water lines comprising exposing biofilms lining dental unit water lines to an effective amount of chlorine dioxide in a manner and for a time effective to reduce microbial growth and microbial population and ultimately, reduce or eliminate the biofilm.

In one embodiment, dental units are decontaminated with an initial exposure (about 10 to about 16 hours) to an effective amount of an aqueous chlorine dioxide or chlorine solution, and thereafter to weekly exposures of an effective amount of a chlorine dioxide containing composition (preferably, about 1000 ppm) for a time and in a manner (preferably, about 30 minutes weekly) which is effective to reduce microbial growth and the size of a biofilm in which the microbes grow. In many instances, the biofilm bacteria may be eliminated after an initial exposure to the chlorine dioxide containing composition. In another embodiment, the units are decontaminated in the same manner by an initial overnight exposure to 1000 ppm, followed by exposure for three consecutive days to a 100–500 (preferably 100) ppm solution of chlorine dioxide on a weekly basis. In other embodiments, the dental units may be decontaminated daily with effective amounts of chlorine dioxide and/or chlorine solutions. In yet another embodiment, after an initial decontamination, a dental unit is fitted to deliver a continuous supply of less than about 1 ppm to about 10 ppm (preferably, up to about 1 ppm) chlorine dioxide solution to the water directed to the patient. And, in a related embodiment, after an initial decontamination or in instances where the dental unit is not yet contaminated, for example, in instances where the unit is new or has recently been repaired or serviced, the dental unit can be put on a maintenance treatment of up to 3–10 ppm of chlorine dioxide, included in the supply water from an external source.

These, and other aspects of this invention will become evident upon reference to the following detailed description.

DETAILED DESCRIPTION OF THE INVENTION

The following terms shall be used to describe the present invention.

The term "chlorine dioxide" is used to describe the chemical compound $ClO_2$. Chlorine dioxide is a potent antimicrobial agent, as well as a bleaching material, in many commercial and industrial applications. It has disinfectant, bleaching and oxidizing properties. $ClO_2$ is a reactive gas which is explosive in air at levels approximating 10%. It is generally produced "on site" by acidification of chlorite solutions, but may be stabilized in certain compositions. Chlorine dioxide compositions, when used in decontamination aspects according to the present invention generally comprise about 25 ppm (preferably at least about 100 ppm) to about 2,500 ppm, more preferably about 500 to about 1,500 ppm, even more preferably about 1,000 ppm of chlorine dioxide and less than about 1 ppm (preferably, at least about 1 ppm) to about 10 ppm in maintenance aspects according to the invention.

The term "small diameter water line" is used throughout the specification to describe water line tubing (which may be made of any material, but is usually made of stainless steel, a copper alloy or a high density plastic) in a delivery system, including dental water lines, which has a small diameter (preferably, less than about 0.75", more often less than about 0.5" or even less than 0.25"), which is generally used in intermittently static water-containing and delivery systems and over time, becomes contaminated with microbial growth which ultimately results in a biofilm on the inside walls of the water lines. In one particularly preferred aspect according to the present invention, the term "small diameter water line" also applies to the piping and reservoir tanks of dental units.

The term "biofilm" is used to describe a microbial film which appears on the inner walls of dental water lines and which is treated (most preferably, removed) using compositions according to the present invention. Biofilms according to the present invention may range in depth from a thin film to rather substantial films (biofilms up to 1 mil thick are not uncommon) and may comprise huge numbers of microorganisms which exist in a film coating the inner walls of small diameter water lines, and such biofilms may vary in length from a short span or small area to, in certain cases, the complete span of a water line.

The term "effective" is used to describe an amount or concentration of an agent such as the composition which contains chlorine dioxide in the present invention or the amount of time used to produce an intended result, the ultimate result being the reduction in microbial flora which are found in biofilms. Consistent with the reduction and/or elimination of microbes, the size of the biofilm is reduced (preferably, and in most instances, the biofilm is completely eliminated from the small diameter water line). For example, in the case of the reduction and/or the complete removal of a biofilm from a water line surface, an effective amount of the composition according to the present invention is that amount which is effective for substantially eliminating microbial growth and in this manner, reducing the thickness and/or the size of the biofilm to a level where it is completely removed. In general, an effective time (also, a sufficient time or sufficient duration) is the amount of time in which a composition according to the present invention is exposed to a biofilm in order to effect reduction in the actual number of microbes within a biofilm. Thus, compositions according to the present invention are used to treat biofilms in an effective amount and for an effective period to reduce and/or eliminate microbial flora in a biofilm, the ultimate result being the reduction in the size and preferably, the elimination of a biofilm from a small diameter water line. In general, chlorine dioxide compositions will range from about 25 to about 2,500 ppm chlorine dioxide in decontamination steps and from less than about 1 ppm (preferably, at least about 1 ppm) to about 10 ppm chlorine dioxide for maintenance steps. In the case of the use of chlorine solutions, which may be used in decontamination steps or maintenance steps in the present invention (along with at least one decontamination or maintenance step which utilizes chlorine dioxide), in decontamination applications effective amounts of chlorine range from about 1000 ppm to 130,000 ppm or more, preferably at least about 5,000 ppm within this range and in maintenance applications effective amounts of chlorine range from about 1 ppm to about 10 ppm, preferably about 1 ppm to about 3 ppm. The terms "continuous" and "continual" within the context of their use, shall mean on a regular, generally daily basis with intermittent cessation for periods for maintenance or non-use.

The term "reduce" or "reduction" shall be used to describe the degree that chlorine dioxide compositions according to the present invention diminish the number of microorganisms which are found in biofilm. The method according to the present invention may be used to reduce the number of microorganisms in biofilm by at least 50%, more preferably at least 75%, even more preferably at least about 90–95%. In certain applications, microbial numbers will be reduced by at least 98+%. It is an unexpected result that compositions according to the present invention will reduce microbial flora in biofilms to such an extent, even with only one treatment. The term "eliminate" or "eliminating" shall mean reducing microbial growth in biofilm to a level of less than about 1% of the original microbial population.

The present invention is generally directed to disinfecting compositions comprising chlorine dioxide which are effective in penetrating bacterial biofilms that develop and populate the inner wall tubing of intermittently static water-containing and delivery systems, and markedly reducing or destroying all microbial populations therein. In preferred aspects, the present invention is particularly directed to the piping and reservoir tanks of dental water units. Biofilms, which form rapidly through a combination of active and passive retractions and colonization by bacteria from the public water systems, can harbor potential pathogens, including protozoa, and may pose particular risk to immunocompromised dental patients. The present invention represents an unexpected result in providing an effective means of reducing and/or eliminating biofilms from small diameter water lines, inasmuch as other common disinfectant methods do not readily reduce and/or eliminate biofilms.

The carbohydrate matrix of the biofilms is of such structure that larger germicidal molecules, such as glutaraldehyde and chlorhexidine cannot effectively penetrate the sponge-like structure of the film to reach and destroy the resident microbes. Chlorine, on the other hand, is a very effective antimicrobial that appears to exert its antimicrobial effect by oxidatively-destroying accessible portions of the carbohydrate-based biofilm, while simultaneously killing the microbes in those sections. Being a strong oxidant, it cannot effectively penetrate the film and selectively destroy the organisms, but oxidizes all exposed organic matter, biofilm and organism. In one facility, 13% (130,000 ppm) hypochlorite has been used periodically to disinfect the dental units, which provides dramatic reductions in bacterial counts, but these rise again rather quickly presumably because the biofilms are not eliminated completely. This is consistent with the finding that biofilm bacteria are 150–3000 times more resistant to hypochlorous acid (free chlorine) than are unattached cells, and that transport of chlorine into the biofilm is the major rate limiting factor in disinfection. Increasing the level of chlorine, even to 130,000 ppm, does not increase disinfection efficiency.

In contrast and unexpectedly, chlorine dioxide ($ClO_2$), which is a comparably small molecule, has the apparent ability to penetrate biofilms with a much greater efficiency and destroy deep-lying bacteria. The probable basis for this penetrability is the lower oxidation potential of $ClO_2$ as cf. the two forms of aqueous chlorine, i.e.

$$HOCl + H^+ + 2e^- \rightarrow Cl^- + H_2O \quad 1.49V$$

$$Cl_2 + 2e^- \rightarrow 2Cl^- \quad 1.36V$$

$$ClO_2 + e^- \rightarrow ClO_2^- \quad 0.95V$$

The lower potential for oxidation allows the $ClO_2$ molecule to diffuse through much of the glycocalyx of the biofilm with little interaction and reductive degradation by the carbohydrate film, and thus reach the protein-bearing surfaces of the bacteria and effect their oxidative destruction. This lower tendency for $ClO_2$ reaction with the glycocalyx, coupled with its high antimicrobial efficacy, is the prime reason why $ClO_2$ may be more effective here.

An expert panel of the American Dental Association has recommended that the dental industry in the US develop methods capable of achieving fewer than 200 ($2 \times 10^2$) cfu/ml in unfiltered water from dental units by the year 2000. Current European Union legislation requires that water emanating from dental water units be of potable quality. The EU requires that total bacterial counts in drinking water be 100 cfu/ml or lower. This is to be compared with current bacterial effluent levels ranging from $10^5$ to $10^7$, primarily stemming from biofilm sources, representing a thousand-fold to hundred thousand-fold higher level than recommended. Typical potable water sources have bacterial levels in the $\sim 10^3$ to $10^5$ cfu/ml range, as a broad generalization, although some municipal water supplies do achieve the $10^2$ cfu/ml level recommended by the various commissions. Practically speaking then, a 100-fold reduction in bacterial levels (i.e. $10^2$ cfu/ml) which reach the dental patient is a practical goal. This represents, in essence, reducing the effluent bacterial levels to that of the incoming water.

The first step in achieving that goal is to destroy the source of the organisms, i.e. the biofilm, responsible for the elevated counts above that of the incoming water. This requires contact with an effective germicide over a sufficient time span to eliminate the bacterial population of the film, if not the film itself. Once that has been accomplished, the water supply should be so treated that redevelopment and/or repopulation of the biofilm is suppressed.

Since biofilms accumulate in virtually all dental water units, but to different degrees depending on the manufacturer and model and the number of individuals using the units in a dentist's office, the following general approach is recommended for both Phase 1, the initial decontamination phase, and Phase 2, the maintenance phase (maintaining bacterial levels comparable to that of the potable supply water). For the initial destruction of organisms resident in the biofilm adhering to the inner surfaces of contaminated dental water units, an aqueous solution of chlorine dioxide ($ClO_2$) in the concentration range of 100 to 1000 parts per million (ppm) is preferred. The contact time and number of decontamination cycles will vary, depending upon the degree of contamination, unit model and manufacturer, and other relevant factors such as microbial counts of the water source and the nature of the bacterial populace. Resident times for the solution will vary from approximately 30 minutes to 24 hours or longer, with a preferred exposure being overnight (e.g. 10 and 16 hours). The $ClO_2$ solution can be generated by any of the standard methods, such as oxidation of a metal chlorite solution by hypochlorite, persulfate, or the like, or reduction of a metal chlorate solution. (See, for example, Massschelein, W. J.; (1979) *Chlorine Dioxde; Chemistry and Environmental Impact of Oxychlorine Compounds*. Ann Arbor Science, Michigan). In a preferred embodiment, the $ClO_2$ is prepared by oxidation of a chlorite solution of such concentration that the molar ratio of residual chlorite to formed $ClO_2$ is ~1:1 to ~20:1 [for example, as disclosed in U.S. Pat. No. 5,993,864, relevant portions of the disclosure of which are incorporated by reference herein]. The chlorine dioxide containing solution may be prepared on site, or delivered from a storage container containing pre-prepared solution. Frequency of application of the phase 1 treatment will generally range from a single treatment, in Dental Water Units (DWU) of lesser biofilm contamination, to a five-cycle treatment for severely contaminated lines. In the latter cases, overnight residence of the $ClO_2$ solution is recommended for each application.

For the phase 2 maintenance phase, a level of $ClO_2$ of up to about 1 ppm is recommended in the water that reaches the patient. In a preferred embodiment, the $ClO_2$ is delivered as a dilution of a concentrate delivered from an external unit with a proportioning device. The $ClO_2$ in that unit may be either prepared directly prior to connecting it into the water line, from an appropriate chemical system, or purchased pre-prepared in certain $ClO_2$-impermeable containers. The degree of $ClO_2$ concentration may range up to several thousand ppm, depending upon such factors as its mode of manufacture, proportioning ratios, stability of the container to $ClO_2$ solutions, and availability of prepackaged material.

The treatment solution may be placed, for example, in the reservoir of the equipment or, in some recent models, into an injection port for that purpose. In a preferred embodiment, the preformed $ClO_2$ solution in a special $ClO_2$-impermeable container comprising glass or a polyethylene terephthalate container (such as those described in U.S. patent application Ser. No. 09/300,505, filed Apr. 28, 1999, entitled "Compositions and Methods for Storing Aqueous Chlorine Dioxide Solutions", relevant portions of which are incorporated by reference herein) adapted to be attached through a special fixture directly to the dental water line, is connected to the line, and allowed to flow into the water through an appropriate toggle switch.

Alternatively, the $ClO_2$ can be generated directly in the reservoir by pre-insertion of the reactive oxychlorine species, e.g. the chlorite, followed by addition of the components necessary to bring about conversion to $ClO_2$, e.g. measured amounts of acid buffering agent and oxidant. This applies for both the phase 1 (decontamination) or phase 2 (maintenance) operations. It is important that the treatment water reach all surfaces of the piping of the equipment which may contain biofilm, including, where appropriate the high-speed drill and the two water-bearing lumens in the so-called three-in-one, i.e. the sucker and the water spray. For phase 1 applications, the $ClO_2$ solution can contain an oxidation-resistant coloring material (e.g. methylene blue) to visually verify that the solution has fully run through the various pipings prior to sealing the system for the desired contact period. In both treatment phases, following application and residence (in phase 1), the $ClO_2$ is flushed from the unit with multiple volumes of water relative to the dead volume of the unit.

To verify the efficacy of both treatments, the effluent and supply waters are then sampled periodically by standard microbiological procedures known to those skilled in the art. In a typical sampling, the waters would be serially diluted and inoculated into the following media:

| | |
|---|---|
| Blood agar | for total anaerobic and aerobic counts |
| Maconkey agar | for coliforms and Pseudomonas |
| SCYE agar | for Legionella |

If the effluent water microbial counts are not comparable to that of the supply water, the $ClO_2$ concentration and/or contact time of the treatment is appropriately increased, and the flushing and evaluation is then repeated.

The concentration of $ClO_2$ to be used in the decontamination phase can range from about 100 ppm to 2,500 ppm, depending on many factors, which include the degree of biofilm build-up, age of the system, make and model of the equipment, relative degree of down-time of the equipment, the microbial population of the biofilm and other characteristics of the supply water (e.g. temperature for preceding period, hardness, organic matter). Residence time of the disinfectant is also dependent on many of the same characteristics, but it is generally preferred to select an overnight exposure, using a $ClO_2$ solution containing about 500 to about 1,500, more preferably about 1,000 ppm of $ClO_2$. If subsequent culturing (measurement) shows organism counts above that of the influent water, the treatment is repeated, at a concentration dependent on the count disparity, and resampling and measurement then repeated. The concentration of $ClO_2$ to be used in the maintenance phase can range up to 1 ppm, consistent with any pertinent federal regulations (e.g. the US Environmental Protection Agency). An alternative maintenance solution for phase 2 is chlorine, in a concentration up to about 3 ppm, which is the level at which chlorine is minimally detectable by taste or smell). This can be achieved, for example, by chlorinating municipal waters which are not already chlorinated or by supplementing those that are, since municipal water chlorination levels generally are lower than 3 ppm. Means of accomplishing such chlorination are well known to those of ordinary skill and fully known to those skilled in the art.

The present invention is illustrated by the following examples, which are to be regarded as illustrative rather than restrictive. Unless otherwise noted, all parts and percentages in the examples, as well as the specification and claims, are by weight.

Example 1

Treatment

This example involved six dental water units, in a preliminary range finding study. The study was run during a particularly warm period of weather, where concomitant warmer municipal water temperatures would be expected to exacerbate biofilm contamination problems. The units were all of the same model, and were fitted with detachable water reservoirs. 100 ml of tap water was placed in each reservoir, and water was then run through the ultrasonic outlets for 30 seconds. Thereafter 30 ml of water was collected aseptically from each outlet. The reservoirs were then disconnected, and water run out of all outlets until the units ran dry. 100 ml of a 1000 ppm treatment solution, prepared as follows, was then placed in each reservoir:

10 ml of a 5.0% sodium chlorite solution was pipetted into a 100-ml volumetric flask already containing 75 ml of deionized water. To that was added 2.0 ml of 13% sodium hypochlorite solution (bleach). Immediately thereafter, 10.0 ml of a 1.9% citric acid solution was added, brought to volume with deionized water, sealed and the flask was agitated to mix the contents.

All outlets were then run until the solution came through each one. The solutions were then left in each unit for 30 minutes, after which the reservoirs were disconnected and the treatment solution was run out until all three outlets from each unit were dry. The reservoirs were then rinsed and filled with water (about 1 liter), and the water then run out of all three outlets until the reservoirs were empty.

Sampling 30 ml samples of water were collected from the ultrasonic outlets 4 hours, and 1, 3 and 7 days after treatment. Samples were also collected from the tap from which water to operate the units was taken.

Microbial Culture

The water samples were vortex mixed, and then diluted in phosphate-buffered saline in two 10-fold dilutions. The samples were then plated onto yeast extract agar by means of a spiral plater. The plates were incubated at 22° C. for four days, after which they were counted.

Results and Discussion

The raw data, and their averages were as follows:

| Microbial Counts for 6 DWUs after 30-min Treatment with 1000 ppm $ClO_2$ vs. Tap Water [in log cfu/ml of water] | | | | |
|---|---|---|---|---|
| | Time following application | | | |
| UNIT NO. | T = 0 | 1 day | 2 days | 3 days |
| 31 | 3.24 | 2.30 | 2.51 | 2.62 |
| 32 | 4.43 | 1.30 | 3.03 | 2.81 |
| 34 | 4.93 | 1.90 | 2.78 | 3.94 |
| 35 | 4.53 | 2.08 | 3.56 | 3.85 |
| 38 | 5.04 | 2.45 | 3.86 | 5.25 |
| 40 | 5.48 | 3.85 | 3.32 | 4.34 |
| MEAN → | 4.61 | 2.31 | 3.18 | 3.80 |
| Tap Water Control | | | | |
| 31 | 3.83 | 4.04 | 3.30 | 3.38 |
| 32 | 4.40 | 2.26 | 4.21 | 3.39 |
| 34 | 3.84 | 2.41 | 3.02 | 3.66 |
| 35 | 3.81 | 1.60 | 2.68 | 3.62 |
| 38 | 2.51 | 3.09 | 3.43 | 3.88 |
| 40 | 4.11 | 4.06 | 3.92 | 3.06 |
| MEAN → | 3.75 | 2.91 | 3.43 | 3.67 |

In this range-finding study, a 2.3 log drop (numerically from 40,700 to 204) in bacterial colonies per ml of effluent water was observed one day after treatment. The water from the DWU at T =0 was over 7 times higher in cfu/ml (0.86 logs) than the tap water, showing that there was biofilm contamination of the lines. After day two, the difference between T=0 was still 1.43 logs, which represents a 27-fold reduction in the effluent's cfu/ml. By day 3, the DWU effluent approximated that of the tap water, rather than being 7-fold higher as in T=0. This "rebound" effect is thought to result from disruption of the biofilm, leading to a rapid growth phase and consequent increased shedding of bacteria into the fluid phase. One should particularly note that the bacterial level in the potable water supply was much in excess of that recommended by the EU (i.e. 5600 vs. 100 cfu/ml) for potable water, and that the 56-fold excess was undoubtedly responsible for some measure of the biofilm contamination, and the inability of one 30-min, 1000 ppm $ClO_2$ treatment to reduce the biofilm problem to any greater degree, or for a longer period.

Example 2

Treatment

This study was run on a dental water unit that apparently had a similar level of biofilm in its lines as in Example 1, during a time that the water supply also had bacterial levels significantly in excess of potable water recommendations. The level, however, is probably typical of the tap water in the UK, where this study was run. In this study three staggered 30-minute exposures to 500 ppm $ClO_2$ solution were made, and counts then made from 1 to 4 days after each treatment. The techniques of treatment and sampling were similar to those described in Example 1. The $ClO_2$ solution was similarly prepared, using half the level of sodium chlorite and hypochlorite initially, after acidification with citric acid.

Results and Discussion

The raw data were as follows:

Microbial Counts for a DWU after Three Staggered 30-min Treatments with 500 ppm $ClO_2$ vs. Tap Water [in log cfu/ml of water]

| Day | Treatment | Unit Microbial Count (cfu/ml) | Supply Water Count (cfu/ml) |
|---|---|---|---|
| 0 |   | 4.58 |   |
|   | ✓ |   |   |
| 1 |   | 2.66 | 3.40 |
| 4 |   | 4.66 | 3.72 |
| 7 |   | 5.83 |   |
|   | ✓ |   |   |
| 8 |   | 3.04 | 2.58 |
| 11 |   | 4.18 |   |
|   | ✓ |   |   |
| 12 |   | 1.60 | 2.38 |
| 15 |   | 3.15 | 3.48 |
| 18 |   | 4.08 | 2.72 |

The water supply had an average aerobic count of 3.57 logs (3687 cfu/ml). After the first treatment the unit's count was reduced by almost 2-logs (1.92), from 4.58 to 2.66 log cfu/ml, corresponding to an 83-fold reduction in organisms in the effluent water. This is particularly notable since the supply water had a higher count (3.40 logs) than the exit water (2.66 logs). Four days after the first treatment, the effluent water level had reverted to approximately the baseline level, about 1-log higher than the supply water, indicating recolonization and multiplication of the biofilm. This was further evident in the 1.17 log increase (15-fold) in microbial counts from day 4 to day 7 after treatment.

Following the second treatment on day 7, the counts in the effluent water again dropped significantly (2.79 logs, or over 600-fold) to a level approximately that of the influent water. At day 11, four days after the second treatment, the effluent counts had increased to 4.18 log cfu/ml, and the unit was treated again. Counts on day 12, one day after the third treatment, were markedly reduced by 2.58 logs (or almost 400 fold). Four days after this treatment the counts, although increased from day 12, remained below the level of the supply water. Finally on day 18, 7 days after the third treatment, the unit's counts returned to the pre-treatment level.

This Example showed that one day after each of the treatments with 500 ppm $ClO_2$, the average microbial count had been reduced by 2.43 logs (270-fold), even with excessively high microbial counts in the supply water. Three days later, the average rebound in microbial counts was only 1.56 logs (36-fold), so that the effects of the $ClO_2$ disinfection were still evident four days after the treatment.

Example 3

Treatment

This study was run on a dental water unit that had a similar level of biofilm in its lines as in the previous Examples, during a time that the water supply also had bacterial levels significantly in excess of potable water recommendations. The level, however, is probably typical of the tap water in the UK, where this study was run. In this study the unit was treated as in Example 2, but on three consecutive days. Samples were taken of both the incoming supply water and from the unit before treatment on each day, with a 500 ppm $ClO_2$ solution for 30-minutes, and also 1, 2 and 5 days after the last treatment. This schedule is represented in the chart below, along with the data derived from each water sample.

Results and Discussion

The raw data were as follows:

Microbial Counts for a DWU after Three Consecutive Day, 30-min Treatments with 500 ppm $ClO_2$ vs. Tap Water [in log cfu/ml of water]

| Day | Treatment | Days Post-Treatment | Unit Count (cfu/ml) | Supply Water (cfu/ml) |
|---|---|---|---|---|
| 1 |   |   | 4.6 | 1.6 |
|   | ✓ |   |   |   |
| 2 |   | 1 | 2.7 | 3.9 |
|   | ✓ |   |   |   |
| 3 |   | 1 + 1 | 1.8 | 2.8 |
|   | ✓ |   |   |   |
| 4 |   | 1 + 1 + 1 | 2.8 | 3.7 |
| 5 |   | 1 + 1 + 2 | 2.3 | 3.1 |
| 8 |   | 1 + 1 + 5 | 3.9 | 2.9 |

There is an 80-fold (1.9-log) reduction of organisms in the water issuing from the unit one day after the first treatment, that level being 1.2 logs below that of the incoming water (i.e. 3.9–2.7). There is a further 8-fold (0.9 log) reduction compared to the previous day, after the second treatment, on day 3. On the two subsequent days (Day 4 and 5) the counts remain below that of the incoming water by 0.9 and 0.8 logs, respectively. Finally, on Day 8, five days after the last treatment, the count in the issuing water rises to 1.0 log higher than the supply water. This presumably occurs because the unit had been acting as a filter, and trapping bacteria, which would account for the rapid rebound. In this case, the residual glycocalyx of the biofilm would provide a ready site for occupancy by the trapped organisms.

Example 4

Treatment

This study was run on a dental water unit that had been supplied with sterile water for a week, after its normal operation with tap water. The intent of the study was to determine if a unit, once disinfected, and not then re-exposed to tap water with excess levels of microorganisms, would show the rebound in organism levels that has been observed in the previous examples. The unit was exposed to a single 1000 ppm solution of $ClO_2$, prepared and applied for 30 minutes, as fully described in Example 1. Sampling and counting techniques were also the same.

Results and Discussion

The raw data were as follows:

Results and Discussion: The raw data were as follows:
Microbial Counts from a DWU Supplied with Sterile Water
After a Single 1000 ppm $ClO_2$ 30-Minute Exposure (X)

| Day | Treatment | Unit Use* | Microbial Counts (log cfu/ml) | |
|---|---|---|---|---|
| | | | Unit Water | Water Supply |
| 0 | | Active | 4.58 | 0 |
| 2 | | Active | 6.00 | 0 |
| 4 | | Active | 3.62 | 0 |
| 7 | | Active | 4.23 | 0 |
| | X | Active | | |
| 8 | | Active | 2.26 | 0 |
| 9 | | Active | 1.3 | 0 |
| 10 | | Active | 1.3 | 0 |
| 11 | | Active | 0 | 0 |
| 12 | | Passive | | |
| 13 | | Passive | | |
| 14 | | Active | 3.88 | 0 |

*Denotes use in weekday operation of dental unit (Active) or inactivity during weekend (Passive)

These data clearly indicate that simply running sterile water through a biofilm-contaminated dental water unit for a week has little effect in reducing the level of microorganisms being introduced into the water from the biofilm populating the lumen of the unit's tubing. Then within a day of applying the $ClO_2$ treatment, the unit drops 2.35 log cfu/ml, from an average of 4.61 logs (40,700 cfu/ml) to 2.26 (182 cfu/ml), a population drop of about 40,500 microbial organism per ml of water. On each of the subsequent 2 days there is a further 10-fold drop to 1.3 logs ( a total drop from the initial 40,500 to 20 organisms per ml) and then, with no further treatment, it continues dropping on the $4^{th}$ day post-application to sterility (0 cfu/ml).

Presumably had the unit not been turned off for the weekend, and continued to be supplied with sterile water, the organism level in the effluent water would have remained near 0. However the stagnation of the water in the unit resulted in the regrowth of residual organism in the remaining biofilm structures, to again produce organism levels in the effluent approximating the pre-test situation. Had the unit been given a $ClO_2$ treatment for 30 minutes on Monday, Day 14, prior to active use, the microbial counts would probably have resumed their low levels, and continued as such for the remainder of the week. This would form the basis for a decontaminating, controlling protocol, to ensure that operatory patients would not be exposed to potentially harmful levels of microorganisms during their dental treatment.

From the foregoing, it will be evident that although specific embodiments of the invention have been described herein for the purpose of illustrating the invention, various modifications may be made without deviating from the spirit and scope of the invention.

We claim:

1. A method of reducing or eliminating microbial flora associated with biofilm in a small diameter dental water line, said method comprising exposing said biofilm to a composition comprising an effective amount of chlorine dioxide within the concentration range of about 500 ppm to about 2500 ppm for a period of at least about 30 minutes to reduce or eliminate said microbial flora.

2. The method according to claim 1 wherein said composition comprises chlorine dioxide within a concentration range of about 500 to about 1500 parts per million of said composition.

3. The method according to claim 1 wherein said composition comprises about 1000 parts per million of chlorine dioxide.

4. The method according to claim 1 wherein said method of reducing or eliminating comprises exposing said biofilm to a composition comprising about 500 to about 1500 parts per million of chlorine dioxide for a period of time ranging from about 30 minutes to about 24 hours.

5. The method according to claim 1 wherein said biofilm is exposed to said composition for a period ranging from about 10 to about 16 hours.

6. A method of reducing microbial flora associated with biofilm in a small diameter dental water line, said method comprising exposing said biofilm to a composition comprising an effective amount of chlorine dioxide within the concentration range of about 500 ppm to about 2500 ppm for a period of at least 30 about minutes to reduce or eliminate said microbial flora.

7. The method according to claim 6 wherein said composition comprises chlorine dioxide within a concentration range of about 500 to about 1500 parts per million of said composition.

8. The method according to claim 6 wherein said composition comprises about 1000 parts per million of chlorine dioxide.

9. The method according to claim 6 wherein said method of reducing or eliminating comprises exposing said biofilm to a composition comprising about 500 to about 1500 parts per million of chlorine dioxide for a period of time ranging from about 30 minutes to about 24 hours.

10. The method according to claim 6 wherein said biofilm is exposed to said composition for a period ranging from about 10 to about 16 hours.

11. A method of reducing an initial population of microbial flora associated with biofilm in a small diameter dental water line and maintaining microbial flora within said biofilm at a reduced population in comparison to said initial population, said method comprising a first decontamination step and a second maintenance step;

wherein said decontamination step comprises exposing said biofilm or said small diameter water line to a composition comprising an effective amount of chlorine dioxide within the concentration range of about 500 ppm to about 2500 ppm for a period of at least about 30 minutes to reduce or eliminate said microbial flora within said biofilm; and wherein said maintenance step comprises exposing said biofilm or said small diameter water line to a composition comprising a maintenance effective amount of chlorine dioxide or chlorine for a period of time and in a manner sufficient to maintain said microbial flora at about said reduced population.

12. The method according to claim 11 wherein said composition used in said decontamination step comprises a concentration of chlorine dioxide ranging from about 500 to about 1500 parts per million.

13. The method according to claim 11 wherein said composition used in said decontamination step comprises about 1000 parts per million of chlorine dioxide.

14. The method according to claim 11 wherein said maintenance step comprises exposing said biofilm or said small diameter water lines to a composition comprising chlorine dioxide in an amount ranging from about 1 to about 10 ppm or chlorine in an amount of about 1 to about 3 ppm on a continual basis.

15. The method according to claim 11 wherein said bioflim is exposed to said composition in said decontamination step for a period ranging from about 10 to about 16 hours.

16. The method according to claim 11 wherein said decontamination step comprises exposing said bioflim to a composition comprising about 500 to about 1500 ppm of chlorine dioxide for a period of time ranging from about 10 hours to about 16 hours, and said maintenance step comprises exposing said bioflim or said small diameter water lines to a composition comprising chlorine dioxide in an amount of about 100 to about 500 ppm for a period of up to three consecutive days on a weekly basis.

17. The method according to claim 11 wherein said composition used in said maintenance step comprises about 100 ppm chlorine dioxide.

* * * * *